United States Patent
Lofgren et al.

[19]

[11] Patent Number: 5,871,015
[45] Date of Patent: Feb. 16, 1999

[54] MAYO STAND COVER

[75] Inventors: Kristina Lofgren, Molnlycke; Tomas Billgren, Kullavik, both of Sweden

[73] Assignee: Molnlycke Health Care AB, Gothenburg, Sweden

[21] Appl. No.: 894,533

[22] PCT Filed: Feb. 20, 1996

[86] PCT No.: PCT/SE96/00223

§ 371 Date: Sep. 18, 1997

§ 102(e) Date: Sep. 18, 1997

[87] PCT Pub. No.: WO96/25907

PCT Pub. Date: Aug. 29, 1996

[30] Foreign Application Priority Data

Feb. 21, 1995 [SE] Sweden .................................. 9500639

[51] Int. Cl.[6] .................................................. A61B 19/00
[52] U.S. Cl. .......................................... 128/849; 128/856
[58] Field of Search ..................................... 128/849–856

[56] References Cited

U.S. PATENT DOCUMENTS

| 3,335,719 | 8/1967 | Boucher . | |
| 3,747,655 | 7/1973 | Hadtke . | |
| 5,151,314 | 9/1992 | Brown | 128/849 |
| 5,170,804 | 12/1992 | Glassman | 128/849 |
| 5,411,036 | 5/1995 | Wilkes | 128/849 |

FOREIGN PATENT DOCUMENTS

WO 94/01051  1/1994  WIPO .

*Primary Examiner*—Michael A. Brown
*Attorney, Agent, or Firm*—Young & Thompson

[57] ABSTRACT

A Mayo stand cover comprises a first and a second liquid-impermeable panel (1 and 2) which are mutually joined along two opposing long edges and a side edge which extends between two opposing ends of the long edges. An absorbent material (4) extends over at least a part of the outer surface of the first panel (1). The first panel (1) includes a pattern of projections (5) formed in the panel material and projecting outwardly from the inside thereof. The pattern includes at least two discrete rows of projections which extend over the full length of the cover parallel with its long edges.

6 Claims, 1 Drawing Sheet

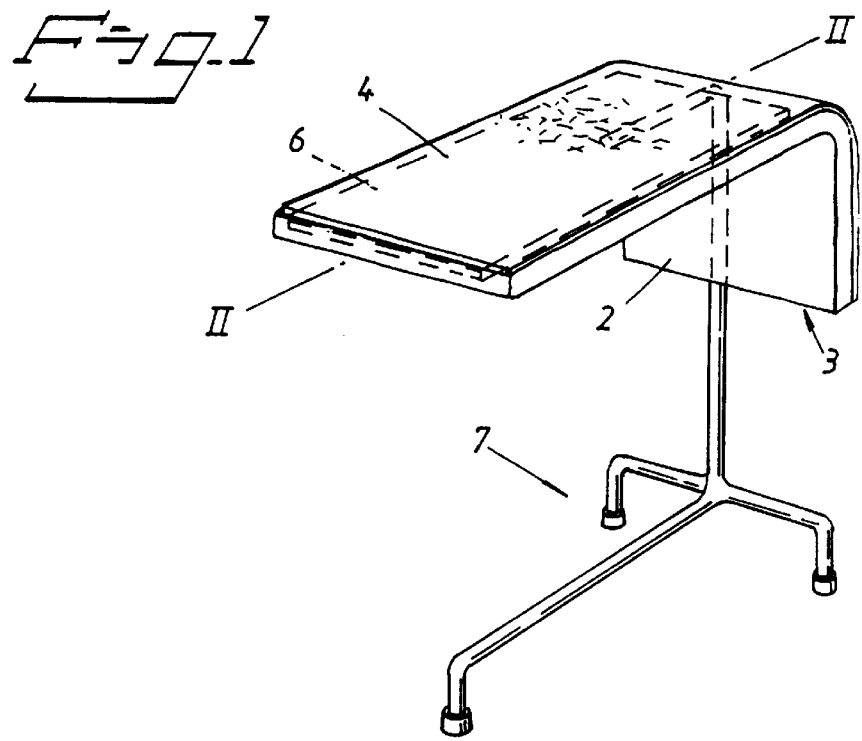
Fig. 1
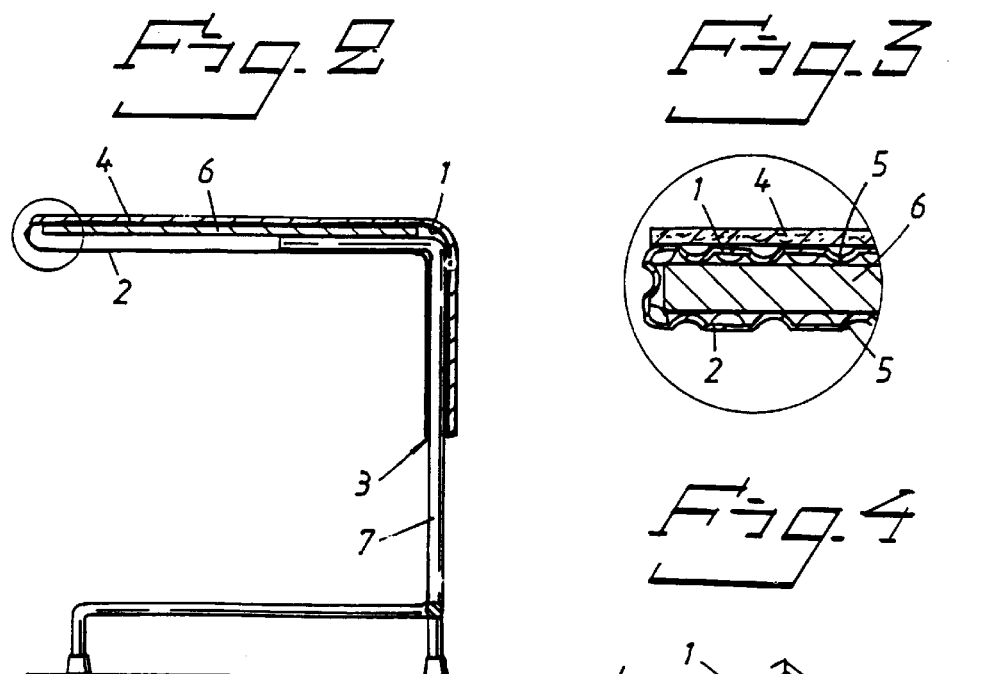
Fig. 2
Fig. 3
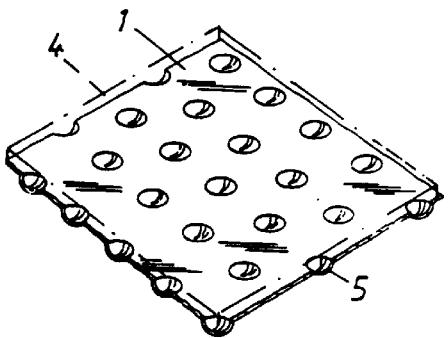
Fig. 4

MAYO STAND COVER

FIELD OF THE INVENTION

The present invention relates to a Mayo stand cover which includes a first and a second liquid-impermeable panel or side, wherein the panels are mutually joined along two opposing long edges and one side edge that extends between two opposing ends of said long edges, and wherein absorbent material is fastened to the outer surface of the first cover panel and extends over at least a part thereof.

BACKGROUND OF THE INVENTION

Mayo stands are used in surgical theatres to hold temporarily instruments and materials, such as bandages, dressings, swabs and surgical drapes used in surgery. These stands may include a table surface which is supported at one short end by an appropriately designed mounting. In order to prevent contamination of the table surface, a Mayo stand cover is fitted over the surface, so that one cover panel will be situated on top of the surface and the other beneath said surface. A layer of absorbent material is placed on the outer surface of the cover panel that lies on top of the table surface when the cover is in use. The absorbent layer is intended to prevent liquid, primarily blood, present on the instruments or the material used in surgery from running along the other panel or splashing down onto the floor. When surgery is completed, the stand cover is used as a trash bag into which disposable material is stowed as the cover is removed and turned inside out in the process, so that the then inwardly facing surfaces of the cover will now face outwards.

Mayo stand covers are normally made of plastic material. One problem encountered with thin plastic covers is that the cover panels tend to stick together, therewith making opening of the covers difficult. Besides the obvious solution of using thicker plastic materials, the problem has been solved by providing the plastic layers with patterns of small homogenous plastic or glass beads which are admixed with the plastic compound prior to extrusion. In addition to making manufacture of the covers more difficult and more expensive, this solution has the drawback that the homogenous beads spread radiation when sterilizing the covers by radiation, so as to require a high radiation dose in order to achieve effective sterilization. Another problem with thin covers is that the cover panels are easily penetrated by sharp instruments that are dropped onto the covered table surface during surgery.

SUMMARY OF THE INVENTION

The object of the present invention is to provide a thin-walled Mayo stand cover which can be opened and fitted over the table surface easily, and with which the risk of the cover being penetrated by sharp instruments for instance is relatively small.

This object is achieved with a Mayo stand cover of the kind defined in the introduction which is characterized in that the first cover panel has formed therein a pattern of projections which extend out from the inside of said panel, wherein the pattern at least includes at least two discrete rows of projections which extend along the full length of the cover parallel with its long edges. This pattern of projections greatly reduces adhesion between the mutually opposing surfaces of the cover panels, therewith enabling the cover to be opened and fitted onto a Mayo stand easily. The projections also distance the cover panel from the table surface and impart a certain degree of suppleness to said panel, which in combination greatly reduces the risk of penetration. These factors also impart a sound-damping property to the stand cover.

In one preferred embodiment, the first cover panel includes a regular pattern of projections which extends over the whole of the panel. In a preferred variant, the second cover panel also includes a regular pattern of projections which extends over the whole of said panel, and the panels are made of mutually the same liquid-impermeable material. The liquid-impermeable material is conveniently comprised of polyethylene of linear low density. The absorbent material extends over at least a third of the outer surface of the first panel and is comprised of nonwoven material.

BRIEF DESCRIPTION OF THE DRAWINGS

The invention will now be described in more detail with reference to the accompanying drawings, in which FIG. 1 is a schematic perspective view of a Mayo stand cover according to one embodiment of the invention, and shows the cover fitted around the table surface of a Mayo stand;

FIG. 2 is a sectional view taken on the line II—II in FIG. 1;

FIG. 3 shows a detail of FIG. 2 in larger scale; and

FIG. 4 is a schematic perspective view of a piece of the cover panel provided with absorbent material and shown in FIGS. 1–3.

DETAILED DESCRIPTION OF THE INVENTION

The Mayo stand cover shown in FIGS. 1–4 includes two mutually similar plastic panels 1 and 2 which are joined together along three edges thereof, ie along two mutually opposing long edges and one side edge, in any suitable manner, such that the free side edges will form a bag opening 3. By long edges is meant here those edges that extend on respective sides of the opening, irrespective of whether these edges are longer than the side edges or not. A layer 4 of absorbent material, preferably nonwoven material, is fixed to the outer surface of the cover panel 1. By outer surface is meant here those surfaces of the panels 1 and 2 that face outwards when the cover is fitted over the table surface of a Mayo stand, i.e. those surfaces which face outwards when the cover is removed from its sterile package.

FIG. 4 illustrates a piece of the cover panel 1 provided with a nonwoven layer 4, which is shown in broken lines for the sake of clarity. As clearly shown in the Figure, the panel 1 includes a pattern of cup-shaped projections 5 which project out inwardly from the inside of the panel, in accordance with the invention. In the illustrated embodiment, the cover panel 2 is provided with a corresponding pattern of projections 5. The patterns of projections cover the whole of the panels 1, 2.

When a Mayo stand cover of this design is removed from its sterile package in order to be fitted over the table surface 6 of a Mayo stand, the mutually facing inner surfaces of the panels 1, 2 will thus each have a pattern of inwardly directed projections 5. These mutually facing surfaces will not therefore stick to one another, therewith enabling the inventive cover to be opened very easily and to be readily fitted over the table surface 6. The illustrated Mayo stand includes a table surface 6 which is supported by a mounting 7 at one short end thereof.

In addition to facilitating opening of the cover, the pattern of projections 5 on the panel 1 greatly reduces the risk of the panel being penetrated or cut by sharp instruments that may be dropped onto the panel. One contributory factor in this regard is that the upper surface of the panel 1 is distanced from the table surface 6 by an extent corresponding to the depth of the projections, meaning that the table surface will not act as a counterpressure surface or anvil surface against a sharp instrument dropped onto the upper surface of the cover. This effect also prevents instruments or other relatively heavy objects dropped onto the panel 1 from coming into contact with the table surface via said panel, therewith preventing the occurrence of disturbing noise that might otherwise occur when relatively heavy objects are dropped onto a planar cover panel that rests on the table surface.

Another advantage afforded by the described inventive Mayo stand cover is that the projections provide diffuse reflection, meaning that the cover will not reflect light emanating from the operating theatre in a disturbing manner, presuming, of course, that the number of projections per surface unit is sufficiently large.

The inventive Mayo stand cover can be readily sterilized, e.g. by gas sterilization or radiation sterilization. With regard to radiation sterilization, only a relatively low radiation dosage need be used, meaning that the plastic material in the covers will be decomposed only to a small degree as a result of radiation sterilization. Because the pattern of projections enable the described Mayo stand cover to be opened easily, the cover panels 1, 2 can be made of any plastic material whatsoever, for instance linear low-density polyethylene (LLD).

After use, i.e. when surgery has been completed, the cover can be turned inside out as it is withdrawn from the table surface, so that the previously outer surfaces of the cover will now face inwards, and the cover can be used as a trash bag for all disposable material used during surgery.

It will be understood that the described and illustrated embodiment can be modified within the scope of the invention. For instance, the projections may have a shape other than the cup-shape shown in the drawings, for instance a conical or frusto-conical shape, or the shape of a full pyramid or truncated pyramid. Neither need the pattern of projections extend over the whole of the cover panel. For instance, it may be sufficient to provide the cover panel with a plurality of patterned sections which extend parallel with the long edges of the cover, from the cover bottom to the cover opening, in order to achieve most of the advantages afforded by the invention. The cover panel that does not support a layer of absorbent material may be planar and need not be made of the same material as the panel which carries an absorbent layer. Absorbent material other than nonwoven material may alternatively be used. Neither is it necessary for the absorbent material to extend along the whole of the panel, since it may be sufficient for the material to extend over at least a third of the length of the cover in order to substantially cover the table surface with absorbent material. The invention is therefore only limited by the contents of the following claims.

We claim:

1. A Mayo stand cover comprising:
    a first and a second liquid-impermeable panel of a thin-walled plastic material, said panels being mutually joined along two opposing long edges;
    a side edge extending between two opposing ends of the long edges;
    a layer of absorbent material extending over at least a part of only the outer surface of the first panel;
    the first panel including a pattern of projections formed in the panel material and projecting outwardly from the inside thereof; and
    the pattern including at least two discrete rows of projections which extend over the full length of the cover parallel with its long edges.

2. The cover according to claim 1, wherein the first cover panel includes a regular pattern of projections which extend over the whole of said panel.

3. The cover according to claim 2, wherein the second cover panel also includes a regular pattern of projections which extend over the whole of said panel.

4. The cover according to claim 1, wherein the panels are made of mutually the same liquid-impermeable material.

5. The cover according to claim 4, wherein the liquid-impermeable material is linear low-density polyethylene.

6. The cover according to claim 1, wherein the absorbent material extends over at least a third of the outer surface of the first cover panel.

* * * * *